(12) United States Patent
Kaufman et al.

(10) Patent No.: US 11,020,286 B2
(45) Date of Patent: Jun. 1, 2021

(54) ABSORBENT ARTICLES WITH VISUALLY DIFFERENT CHASSIS AND WAISTBANDS

(71) Applicant: Kimberly-Clark Worldwide, Inc., Neenah, WI (US)

(72) Inventors: Ross T. Kaufman, Appleton, WI (US); Kelly D. Farmer, Neenah, WI (US); Joseph D. Coenen, Kaukauna, WI (US); Jerry L. Hameister, Neenah, WI (US)

(73) Assignee: KIMBERLY-CLARK WORDWIDE, INC., Neenah, WI (US)

( * ) Notice: Subject to any disclaimer, the term of this patent is extended or adjusted under 35 U.S.C. 154(b) by 0 days.

(21) Appl. No.: 16/326,249

(22) PCT Filed: Dec. 19, 2017

(86) PCT No.: PCT/US2017/067362
§ 371 (c)(1),
(2) Date: Feb. 18, 2019

(87) PCT Pub. No.: WO2019/125415
PCT Pub. Date: Jun. 27, 2019

(65) Prior Publication Data
US 2019/0358093 A1   Nov. 28, 2019

(51) Int. Cl.
*A61F 13/49* (2006.01)

(52) U.S. Cl.
CPC .. *A61F 13/49061* (2013.01); *A61F 13/49011* (2013.01); *A61F 2013/49026* (2013.01)

(58) Field of Classification Search
CPC .......... A61F 13/49011; A61F 13/49012; A61F 13/49019; A61F 13/4902; A61F 13/49061;
(Continued)

(56) References Cited

U.S. PATENT DOCUMENTS

| 6,291,039 B1 | 9/2001 | Combe et al. |
| 7,582,348 B2 | 9/2009 | Ando et al. |

(Continued)

FOREIGN PATENT DOCUMENTS

| JP | 2009056156 A | 3/2009 |
| JP | 2016022235 A | 2/2016 |

(Continued)

*Primary Examiner* — Catharine L Anderson
*Assistant Examiner* — Lynne Anderson
(74) *Attorney, Agent, or Firm* — Kimberly-Clark Worldwide, Inc.

(57) ABSTRACT

Exemplary wearable articles including regions with differing visual patterns are disclosed. In one embodiment, an article may comprise an elasticated front chassis region and an elasticated front waistband region, a rear region, a crotch region, and an absorbent body disposed at least partially within the crotch region. The front chassis and front waistband regions may comprise a plurality of elastomeric strands disposed between a first material and a material and are bonded together by a plurality of discrete bonds, at least some of which entrap the strands. The strands of the front chassis region are spaced apart a first distance, while the strands of the front waistband region are spaced apart a second distance, with the second distance being less than the first distance.

9 Claims, 5 Drawing Sheets

(58) Field of Classification Search
CPC .. A61F 2013/49025; A61F 2013/49026; A61F 2013/49028; A61F 2013/49031; A61F 2013/49036
See application file for complete search history.

(56) References Cited

U.S. PATENT DOCUMENTS

| | | | | |
|---|---|---|---|---|
| 8,282,617 | B2* | 10/2012 | Kaneda | A61F 13/49011 604/393 |
| 8,647,319 | B2 | 2/2014 | Een et al. | |
| 9,107,777 | B2* | 8/2015 | Kinoshita | A61F 13/49011 |
| 2005/0095942 | A1 | 5/2005 | Mueller et al. | |
| 2008/0161768 | A1* | 7/2008 | Baba | A61F 13/15593 604/385.27 |
| 2013/0324956 | A1 | 12/2013 | Zink et al. | |
| 2014/0221956 | A1 | 8/2014 | Martynus et al. | |
| 2015/0328056 | A1 | 11/2015 | Een et al. | |
| 2016/0058624 | A1 | 3/2016 | Hohm et al. | |
| 2016/0159062 | A1 | 6/2016 | Sablone | |
| 2016/0228305 | A1 | 8/2016 | Gualtieri et al. | |
| 2016/0288407 | A1 | 10/2016 | Ehlert et al. | |
| 2016/0331600 | A1 | 11/2016 | Polidori et al. | |
| 2017/0000660 | A1 | 1/2017 | Wade et al. | |
| 2017/0105884 | A1 | 4/2017 | Wade et al. | |
| 2019/0374392 | A1* | 12/2019 | Ninomiya | A61F 13/15 |
| 2019/0374398 | A1* | 12/2019 | Coenen | A61F 13/49015 |

FOREIGN PATENT DOCUMENTS

| | | |
|---|---|---|
| KR | 20120018286 A | 3/2012 |
| KR | 101454048 B1 | 10/2014 |
| WO | 07099493 A1 | 9/2007 |
| WO | 2008041639 A1 | 4/2008 |
| WO | 2018160207 A1 | 9/2018 |
| WO | 2018160208 A1 | 9/2018 |

* cited by examiner

ABSORBENT ARTICLES WITH VISUALLY DIFFERENT CHASSIS AND WAISTBANDS

TECHNICAL FIELD

The present disclosure relates to wearable articles including elasticated chassis and waistbands, and more specifically to wearable articles including elasticated chassis and waistbands that have visually different patterns.

BACKGROUND OF THE DISCLOSURE

Elasticated materials are used in many different applications, including within various wearable clothing garments and absorbent articles. Such elasticated materials may be used as part of a chassis, waistbands, leg cuffs, barrier cuffs, or in other components of clothing garments and absorbent articles to provide beneficial fit characteristics, help prevent leakage of bodily exudates, or impart other benefits.

Many present clothing garments and absorbent articles include elasticated materials which comprise elastic strands positioned between layers of material and affixed to the layers of material with adhesive. Some prior art elasticated materials have attempted to remove the adhesive in favor of affixing the elastic strands to the layers of material with the use of discrete individual bonds. These prior art materials position the bonds across the elastic strands a distance less than the un-tensioned diameter of the elastic strands. Some example prior art materials can be seen in U.S. Pat. No. 6,291,039 to Cera France Compagnie d'Equipment Robotique Appliquee, titled "Ruffling Slide and Method for Making Same". This particular structural configuration holds the elastic strands in place within the elasticated material between the bonds. These adhesive-less elasticated materials have a cost advantage as they do not require adhesive to affix the elastomeric strands within the elasticated material. Accordingly, additional elasticated materials which do not include adhesive may be desired to help reduce overall costs of absorbent articles, in addition to having functional or aesthetic benefits.

SUMMARY OF THE DISCLOSURE

The present disclosure relates to absorbent article including elasticated chassis and waistbands, and more specifically to absorbent articles including elasticated chassis and waistbands that have visually different patterns. In general, the chassis and waistbands of the articles of the present disclosure are constructed without adhesive and such that one or more properties of the chassis and waistband differ so as to produce visually different patterns between the waistband and the chassis. For instance, a chassis region of an article of the present disclosure may comprise a plurality of elastomeric strands and be constructed in such a fashion to produce a relatively indistinctly patterned structure, while a waistband of the article may also comprise a plurality of elastomeric strands but be constructed in such a fashion to produce a well-defined patterned structure, allowing a wearer to easily identify the different portions of the article.

In a first embodiment, an absorbent article may extend in a longitudinal direction and in a lateral direction, and the absorbent article may comprise a front region having a front waist edge and comprising an elasticated front chassis region and an elasticated front waistband region, a rear region having a rear waist edge, a crotch region extending between the front region and the rear region, and an absorbent body disposed at least partially within the crotch region. The elasticated front chassis region may further comprise a plurality of elastomeric strands disposed between a first front chassis web material and a second front chassis web material, wherein the first front chassis web material may be bonded to the second front chassis web material by a plurality of discrete bonds, at least some of the discrete bonds forming bond pairs disposed on opposite sides of an elastomeric strand of the plurality of elastomeric strands of the elasticated front chassis region and spaced apart in the longitudinal direction a distance less than an un-tensioned diameter of the elastomeric strand. Further, the plurality of elastomeric strands of the elasticated front chassis region may be spaced apart in the longitudinal direction a first distance. The elasticated front waistband region then may comprise a plurality of elastomeric strands disposed between a first front waistband web material and a second front waistband web material, while the first front waistband web material is bonded to the second front waistband web material by a plurality of discrete bonds, at least some of the discrete bonds forming bond pairs disposed on opposite sides of an elastomeric strand of the plurality of elastomeric strands of the elasticated front waistband region and spaced apart in the longitudinal direction a distance less than an un-tensioned diameter of the elastomeric strand. Finally, the plurality of elastomeric strands of the elasticated front waistband region may be spaced apart in the longitudinal direction a second distance, the second distance being less than the first distance.

In a second embodiment, the second distance of the first embodiment may be less than or equal to 8 mm.

In a third embodiment, the second distance of any of the first or second embodiments may be less than or equal to 6.5 mm.

In a fourth embodiment, the first distance of any of the first through third embodiments may be greater than the second distance by at least 1 mm.

In a fifth embodiment, the plurality of elastomeric strands of the elasticated front waistband region of any of the first through fourth embodiments may have a lower installed elongation than the plurality of elastomeric strands of the elasticated front chassis region.

In a sixth embodiment, the installed elongation of the plurality of elastomeric strands of the elasticated front waistband region of the fifth embodiment may be less than 200%.

In a seventh embodiment, the installed elongation of the plurality of elastomeric strands of the elasticated front chassis region of the sixth embodiment may be greater than the installed elongation of the plurality of elastomeric strands of the elasticated front waistband region by at least 50%.

In an eighth embodiment, the plurality of elastomeric strands of the elasticated front waistband region of any of the first through seventh embodiments may have a higher installed elongation than the plurality of elastomeric strands of the elasticated front chassis region.

In a ninth embodiment, the installed elongation of the plurality of elastomeric strands of the elasticated front chassis region of the eighth embodiment may be less than 200%.

In a tenth embodiment, the installed elongation of the plurality of elastomeric strands of the elasticated front waistband region of the ninth embodiment may be higher than the installed elongation of the plurality of elastomeric strands of the elasticated front chassis region by at least 50%.

In an eleventh embodiment, the plurality of discrete bonds of any of the first through tenth embodiments bonding the first front chassis web material to the second front chassis web material may form a series of rows of bonds and the average distance between longitudinally adjacent rows of bonds within the front chassis region is less than 6 mm.

In a twelfth embodiment, the plurality of bonds of any of the first through eleventh embodiments bonding the first front chassis web material to the second front chassis web material may form a series of bond rows, wherein a plurality of bonds within a first bond row may comprise longitudinally extending side portions which form first angles with respect to the lateral direction, and a plurality of bonds within a second bond row may comprise longitudinally extending side portions which form second angles with respect to the lateral direction where the first angle is different than the second angle.

In a thirteenth embodiment, the second angle of the twelfth embodiment may have a value in degrees that is 180 minus the value of the first angle.

In a fourteenth embodiment, an absorbent article may extend in a longitudinal direction and in a lateral direction and comprise a front region having a front waist edge and comprising an elasticated front chassis region and an elasticated front waistband region, a rear region having a rear waist edge, a crotch region extending between the front region and the rear region, and an absorbent body disposed at least partially within the crotch region. Additionally, the elasticated front chassis region may comprise a plurality of elastomeric strands disposed between a first front chassis web material and a second front chassis web material, where the first front chassis web material is bonded to the second front chassis web material by a plurality of discrete bonds, at least some of the discrete bonds forming bond pairs disposed on opposite sides of an elastomeric strand of the plurality of elastomeric strands of the elasticated front chassis region and spaced apart in the longitudinal direction a distance less than an un-tensioned diameter of the elastomeric strand. Further, the plurality of elastomeric strands of the elasticated front chassis region may be spaced apart in the longitudinal direction a first distance. The elasticated front waistband region may comprise a plurality of elastomeric strands disposed between a first front waistband web material and a second front waistband web material, where the first front waistband web material is bonded to the second front waistband web material by a plurality of discrete bonds, at least some of the discrete bonds forming bond pairs disposed on opposite sides of an elastomeric strand of the plurality of elastomeric strands of the elasticated front waistband region and spaced apart in the longitudinal direction a distance less than an un-tensioned diameter of the elastomeric strand. The plurality of elastomeric strands of the elasticated front waistband region may be spaced apart in the longitudinal direction a second distance, the second distance being less than the first distance, and the installed elongation of the plurality of elastomeric strands of the elasticated front waistband region may be higher than the installed elongation of the plurality of elastomeric strands of the elasticated front chassis region.

In a fifteenth embodiment, the installed elongation of the plurality of elastomeric strands of the elasticated front waistband region of the fourteenth embodiment may be greater than 150%.

In a sixteenth embodiment, the installed elongation of the plurality of elastomeric strands of the elasticated front waistband region of any of the fourteenth or fifteenth embodiments may be greater than 200%.

In a seventeenth embodiment, the installed elongation of the plurality of elastomeric strands of the elasticated front waistband region of any of the fourteenth through sixteenth embodiments may differ from the installed elongation of the plurality of elastomeric strands of the elasticated front chassis region by at least 50%.

In an eighteenth embodiment, the decitex of the plurality of elastomeric strands of the elasticated front waistband region of any of the fourteenth through seventeenth embodiments may be greater than the decitex of the plurality of elastomeric strands of the elasticated front chassis region.

In a nineteenth embodiment, the second distance of any of the fourteenth through eighteenth embodiments may be less than or equal to 6.5 mm.

In a twentieth embodiment, an array of absorbent articles may comprise a first series of absorbent articles comprising a front region having a first front waist edge and comprising an elasticated first front chassis region, a first rear region having a first rear waist edge, a first crotch region extending between the first front region and the first rear region, and a first absorbent body disposed at least partially within the first crotch region. The elasticated first front chassis region may comprise a first plurality of elastomeric strands disposed between a first front chassis web material and a second front chassis web material of the elasticated first front chassis region, where the first front chassis web material of the elasticated first front chassis region is bonded to the second front chassis web material of the elasticated first front chassis region by a plurality of discrete bonds, at least some of the discrete bonds forming bond pairs disposed on opposite sides of an elastomeric strand of the plurality of elastomeric strands of the elasticated first front chassis region and spaced apart in the longitudinal direction a distance less than an un-tensioned diameter of the elastomeric strand. Additionally, the plurality of elastomeric strands of the elasticated first front chassis region may be spaced apart in the longitudinal direction a first distance. The array may further include a second series of absorbent articles comprising a second front region having a second front waist edge and comprising an elasticated second front chassis region, a second rear region having a second rear waist edge, a second crotch region extending between the second front region and the second rear region, and a second absorbent body disposed at least partially within the second crotch region. The elasticated second front chassis region may comprise a plurality of elastomeric strands disposed between a first front chassis web material and a second front chassis web material of the elasticated second front chassis region, where the first front chassis web material of the elasticated second front chassis region is bonded to the second front chassis web material of the elasticated second front chassis region by a plurality of discrete bonds, at least some of the discrete bonds forming bond pairs disposed on opposite sides of an elastomeric strand of the plurality of elastomeric strands of the elasticated second front chassis region and spaced apart in the longitudinal direction a distance less than an un-tensioned diameter of the elastomeric strand. The plurality of elastomeric strands of the elasticated second front chassis region may be spaced apart in the longitudinal direction a second distance, and the second distance may be greater than the first distance by at least 2 mm The above summary of the present disclosure is not intended to describe each embodiment or every implementation of the present disclosure. Advantages and attainments, together with a more complete understanding of the disclosure, will become apparent and appreciated by referring to the following detailed description and claims taken in conjunction with the accompanying drawings.

BRIEF DESCRIPTION OF DRAWINGS

The disclosure may be more completely understood in consideration of the following detailed description of various embodiments in connection with the accompanying drawings, in which.

Figure 1:
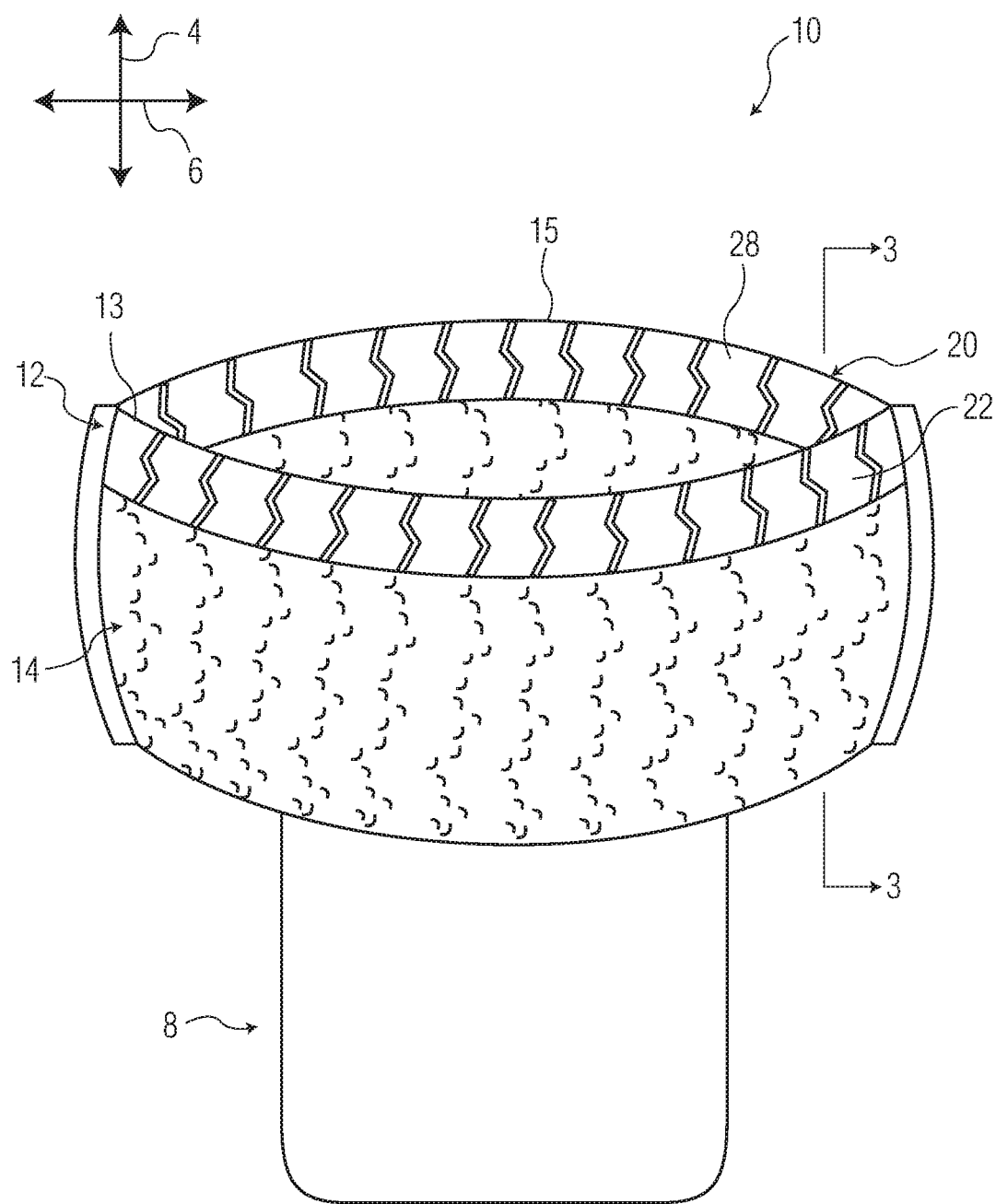
FIG. 1 is a perspective view of an exemplary wearable article in a closed configuration according to aspects of the present disclosure.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the scope of the disclosure.

DETAILED DESCRIPTION OF THE DISCLOSURE

The present disclosure is generally directed toward wearable articles such as absorbent and clothing articles including elasticated chassis and waistbands that have visually different patterns. The chassis and waistbands of such articles of the present disclosure may comprise elastomeric strands which are affixed to the article without adhesive. One or more of the properties of the chassis and waistbands are chosen to be different in order to produce a visually different pattern between the chassis and the waistbands. A potential wearer, in evaluating an article for potential purchase, may take notice of the visually different patterns and thereby easily understand that the product has both an elasticated chassis and an elasticated waistband. The potential user may have greater confidence that such articles fit better than other products which do not have both an elasticated chassis and an elasticated waistband or for which there is no visual difference between the two article regions. The present disclosure details a number of different ways in which a visually different pattern may be produced in materials which do not use adhesive to affix elastomeric strands.

Each example is provided by way of explanation and is not meant as a limitation. For example, features illustrated or described as part of one embodiment or figure can be used on another embodiment or figure to yield yet another embodiment. It is intended that the present disclosure include such modifications and variations.

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions:

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, adult diapers and pants, medical garments, surgical pads and bandages, other personal care or health care garments, and the like without departing from the scope of the present disclosure.

The term "bonded", "attached" or "coupled" refers herein to the joining, adhering, connecting, attaching, or the like, of two elements. Two elements will be considered bonded, attached or coupled together when they are joined, adhered, connected, attached, or the like, directly to one another or indirectly to one another, such as when each is directly bonded to intermediate elements. The bonding, attaching or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives.

The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer liquids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, hydroentangling processes, etc.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "elasticated" when used herein to describe a material or a portion of an article means that the material or article it is made of an inelastic sheet material coupled to elastomeric material, e.g. one or more elastomeric bands or strands, such that the material or article exhibits elastic properties.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Figure 2:
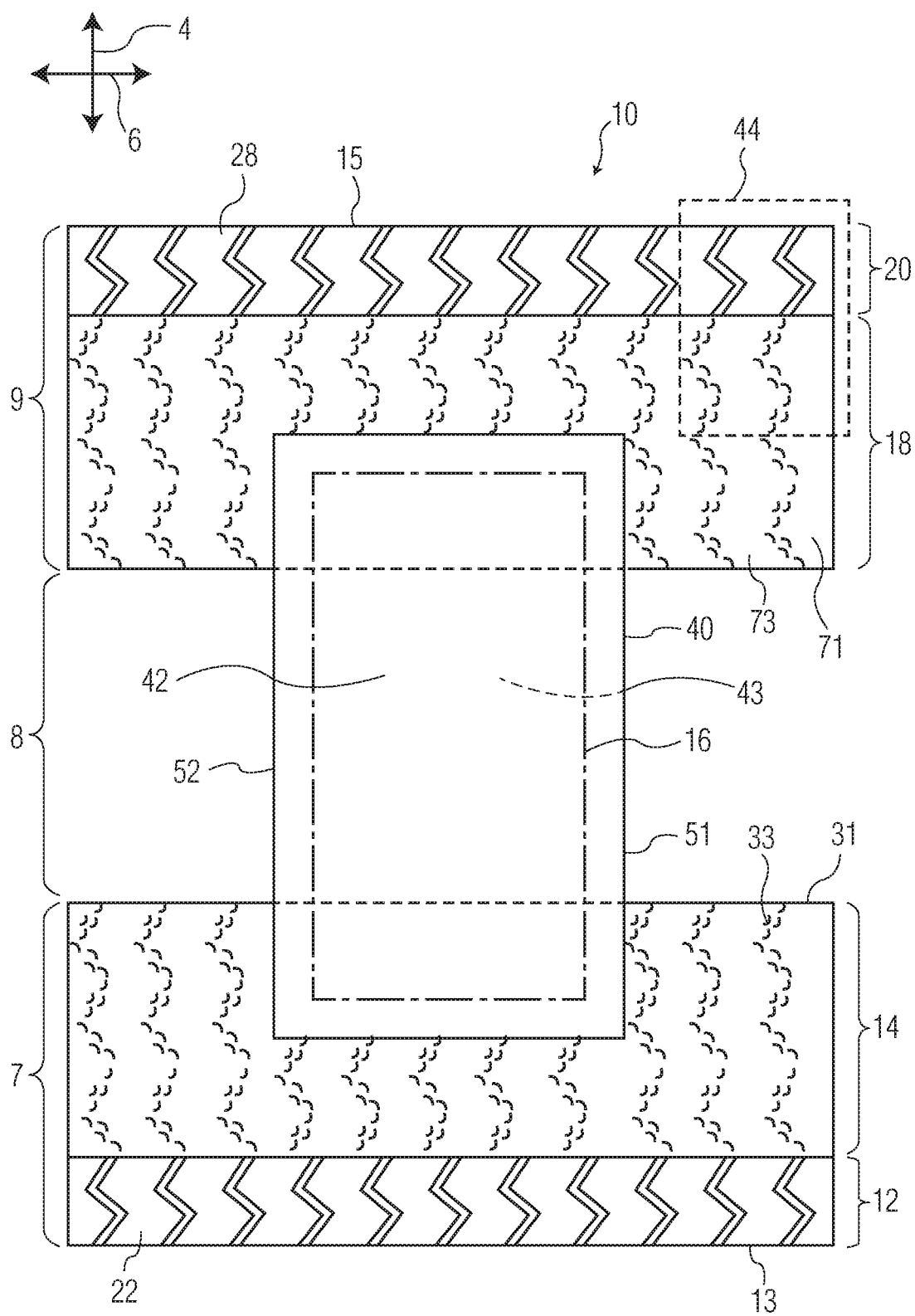
FIG. 2 is a plan view of the article of FIG. 1 in a fully open and laid-flat configuration.

FIG. 1 is a perspective view of exemplary wearable article 10 disposed in a wear configuration, according to the present disclosure. The article 10 includes a front waistband region 12 comprising a front waistband 22, a front chassis region 14, a rear chassis region 18 (as seen in FIG. 2), and a rear waistband region 20 comprising a rear waistband 28, as well as a crotch region 8. As can be seen, the front and rear chassis regions 14, 18 comprise a visually different pattern than the front and rear waistband regions 12, 20. For instance, the front and rear waistband regions 12, 20 may comprise a relatively sharp, definite pattern, whereas the front and rear chassis regions 14, 18 may comprise a relatively indistinct, blousy pattern. Such visual differences may highlight to a potential wearer the presence of separate chassis 14, 18 and waistband 22, 28 components on the article 10. The presence of both such components may give the potential wearer confidence that the article 10 will fit more securely and/or comfortably than articles which do not have a separate waistband component, or for which there is little to no visual distinction between the chassis and the waistband (therefore making it difficult to discern whether a waistband component is part of such an article).

The chassis regions 14, 18 and the waistband regions 12, 20 are elasticated in order to provide a secure and comfortable fit for a wearer. The elastic properties of the regions 12, 14, 18, and 20 are formed through elastomeric strands 23, 24 disposed throughout the chassis regions 14, 18 and the waistband regions 12, 20. These elastomeric strands 23, 24 of the articles 10 are secured within the articles 10 without the use of adhesive. Instead, the elastomeric strands 23, 24 are entrapped between bonds formed throughout the front and rear chassis regions 14, 18 and the front and rear waistband regions 12, 20. For instance, the elastomeric strands 23, 24 may be positioned between one or more web materials of the front and rear chassis regions 14, 18 and the front and rear waistband regions 12, 20 in a stretched manner. Bond pairs are then formed close to the elastomeric strands 23, 24 but on opposing sides of the strands 23, 24. When the elastomeric strands 23, 24 are allowed to relax, their diameters increase to an un-tensioned diameter. However, the portions of the elastomeric strands 23, 24 disposed between the bond pairs are prevented from increasing in diameter and are thereby trapped between the bond pairs. These entrapped portions of the elastomeric strands 23, 24 affix the elastomeric strands 23, 24 within the front and rear waistband regions 12, 20 and the front and rear chassis regions 14, 18. This entrapping of the elastomeric strands 23, 24 will be described in more detail below.

According to aspects of the present disclosure, it has been found that by varying one or more parameters of the chassis regions 14, 18 and/or the front and rear waistband regions 12, 20, visual patterns of differing distinctiveness may be formed. For example, it has been found that the particular spacing between adjacent elastomeric strands 23, 24 affects the definiteness of any visual pattern, as does differing installed elongation of the strands 23, 24, along with the material of the regions 12, 14, 18, 20, the decitex of the strands 23, 24, and parameters of the bonds bonding the materials of the regions 12, 14, 18, and 20. Accordingly, exemplary articles 10 of the present disclosure are described below that combine variations in these parameters in order to produce differing visual patterns between the front and rear chassis regions 14, 18 and the front and rear waistband regions 12, 20 in order to highlight to a potential wearer the presence of both such product features.

FIG. 1 should further be understood to depict only one contemplated exemplary absorbent article 10. Other contemplated articles of the present disclosure may have the front and rear chassis regions 14, 18 comprising the relatively sharp, definite pattern, while the front and rear waistband regions 12, 20 comprise the less distinct, blousy pattern. Even further contemplated embodiments may have the front chassis region 14 comprise the relatively sharp, definite pattern with the front waistband region 12 comprises the less distinct, blousy pattern, while the patterns are reversed for the rear chassis region 18 and the rear waistband region 20. Alternatively, the front chassis region 14 may comprise the less distinct, blousy pattern while the front waistband region 12 comprises the relatively sharp, definite pattern, and these patterns may be reversed for the rear chassis region 18 and the rear waistband region 20.

FIG. 2 is a top-down view of exemplary absorbent article 10 of FIG. 1 in a fully open and laid-flat configuration. Article 10 can be seen extending in the longitudinal direction 4 and the lateral direction 6 and can be broken down in to a front region 7, a crotch region 8, and a rear region 9. Each of the regions 7, 8, 9 may comprise one-third of an overall length of the article 10. The front region 7 and the rear region 9 may comprise at least a portion of the front chassis region 14 and the front waistband region 12, and at least a portion of the rear chassis region 18 and the rear waistband region 20, respectively. Specifics of the different regions 12, 14, 18, and 20 are detailed below with respect to FIGS. 3A and 3B.

Article 10 further comprises a body facing surface 42 and a garment facing surface 43. Where the article 10 comprises an absorbent article, the body facing surface 42, particularly at least throughout the crotch region 7, may generally comprise a bodyside liner material. Such a bodyside liner material can be used to isolate the wearer's skin from liquid waste retained by the article 10. In general, the bodyside liner material can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner material. The bodyside liner material can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner material need not be a unitary layer structure, and thus, can include more than one layer of fabrics, films, and/or webs, as well as combinations thereof. For example, the bodyside liner material can include a support layer and a projection layer that can be hydroentagled. The projection layer can include hollow projections, such as those disclosed in U.S. Pat. No. 9,474,660 to Kirby et al.

For example, the bodyside material can be composed of a meltblown or spunbond web of polyolefin fibers. Alternatively, the bodyside liner material can be a bonded-carded web composed of natural and/or synthetic fibers. The bodyside liner material can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner material or it can be selectively applied to particular sections of the bodyside liner material.

In various embodiments, a bodyside liner material can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner material can be a spunbond substrate with a basis weight from about 10 or 12 to about 15 or 20 gsm. In an embodiment, a bodyside liner material can be a 12 gsm spunbond-meltblown-spunbond substrate having 10% meltblown content applied between the two spunbond layers.

The garment facing surface 43 may generally be formed by an outer cover material. The outer cover material may be, partially or wholly, breathable and/or liquid impermeable and at least some portions may be elastic, stretchable, or non-stretchable, in different embodiments. The outer cover material may be constructed of a single layer in some embodiments and multiple layers in other embodiments, for instance where the outer cover material comprises one or more laminates of materials. The outer cover material may comprise spunbond fabrics, films, meltblown fabrics, elastic netting, microporous webs, bonded-carded webs, and/or foams provided by elastomeric or polymeric materials.

In some contemplated embodiments, the outer cover material can be a single layer of a liquid impermeable material, such as a polymeric film. In further embodiments, the outer cover material can be a multi-layered laminate in which at least one of the layers is liquid impermeable. In some embodiments, the outer cover material can be a two layer construction, including an outer layer (not shown) and an inner layer (not shown) which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

In embodiments where the outer cover material includes multiple layers, the outer layer of the outer cover material can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer of an outer cover 18 can be a 20 gsm spunbond polypropylene non-woven web. The outer layer may also be constructed of the same materials from which the bodyside liner material can be constructed, as described herein, and it also may be apertured to enhance evaporation of urine in the event the inner layer is vapor permeable. In some embodiments, the outer cover material, or at least the outer layer of the outer cover material where the outer cover material is a multi-layer construction, can be embossed and/or matte finished to provide a more cloth-like texture or appearance.

At least one of the inner layers of the outer cover material (or the liquid impermeable outer cover material where the outer cover material is of a single-layer construction) is liquid impermeable and can be either vapor permeable (i.e., "breathable") or vapor impermeable. The liquid impermeable inner layer (or the liquid impermeable outer cover material where the outer cover material is of a single-layer construction) can be manufactured from a thin plastic film. The liquid impermeable inner layer (or the liquid impermeable outer cover material where the outer cover material is of a single-layer construction) can inhibit liquid body exudates from leaking out of the absorbent article 10 and wetting articles, such as bed sheets and clothing, as well as the wearer and caregiver. As some particular examples, the outer cover material can be constructed of a microporous polymeric film, such as polyethylene or polypropylene, or a non-woven material which has been coated or otherwise treated to impart a desired level of liquid impermeability.

In embodiments where the article 10 is a disposable absorbent article, the article 10 further comprises an absorbent body 16 disposed between the body facing surface 42 and the garment facing surface 43. The absorbent body 16 can be suitably constructed to be generally compressible, conformable, pliable, non-irritating to the wearer's skin and capable of absorbing and retaining liquid body exudates. The absorbent body 16 can be manufactured in a wide variety of sizes and shapes (for example, rectangular, trapezoidal, T-shape, I-shape, hourglass shape, etc.) and from a wide variety of materials. The size and the absorbent capacity of the absorbent body 16 should be compatible with the size of the intended wearer (infants to adults) and the liquid loading imparted by the intended use of the absorbent article 10. The absorbent body 16 can have a length and width that can be less than or equal to the length and width of the absorbent article 10.

In some embodiments, the absorbent body 16 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In at least one embodiment, the absorbent body 16 can be a matrix of cellulosic fluff and superabsorbent material. In various embodiments, the absorbent body 16 may be constructed of a single layer of materials, or in the alternative, may be constructed of two or more layers of materials.

Various types of wettable, hydrophilic fibers can be used in the absorbent body 16. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 16 can be free of superabsorbent material or in an alternate embodiment be comprised entirely of superabsorbent material.

The article 10 depicted in FIGS. 1 and 2 comprises a three-piece construction configuration. For example, the front chassis region 14 and the front waistband region 12 form a front waist panel while the rear chassis region 18 and the rear waistband region 20 form a rear waist panel. The article 10 further comprises an absorbent panel 40 extending between the front waist panel and the rear waist panel. The absorbent panel 40 can have a first lateral side edge 51 and a second lateral side edge 52 and can overlap the front waist panel and the rear waist panel. The absorbent panel 40 can further be bonded to the front waist panel and the rear waist panel to define a three-piece construction. However, it is contemplated that an absorbent article can be manufactured in a CD process without being a three-piece construction garment, which is also sometimes referred to as a one-piece construction (not shown), as the front waist panel and the rear waist panel are integral with one another by way of commonly connected components forming the waist panels such as a bodyside liner and/or an outer cover which can envelope the absorbent panel 40 or simply cover the garment side of the absorbent panel 40. However, articles having the described elasticated regions with differing visual patterns that are contemplated by the present disclosure may be formed according to any suitable methods. CD processes are only one contemplated way to form such articles 10 of the present disclosure.

Figure 3A:
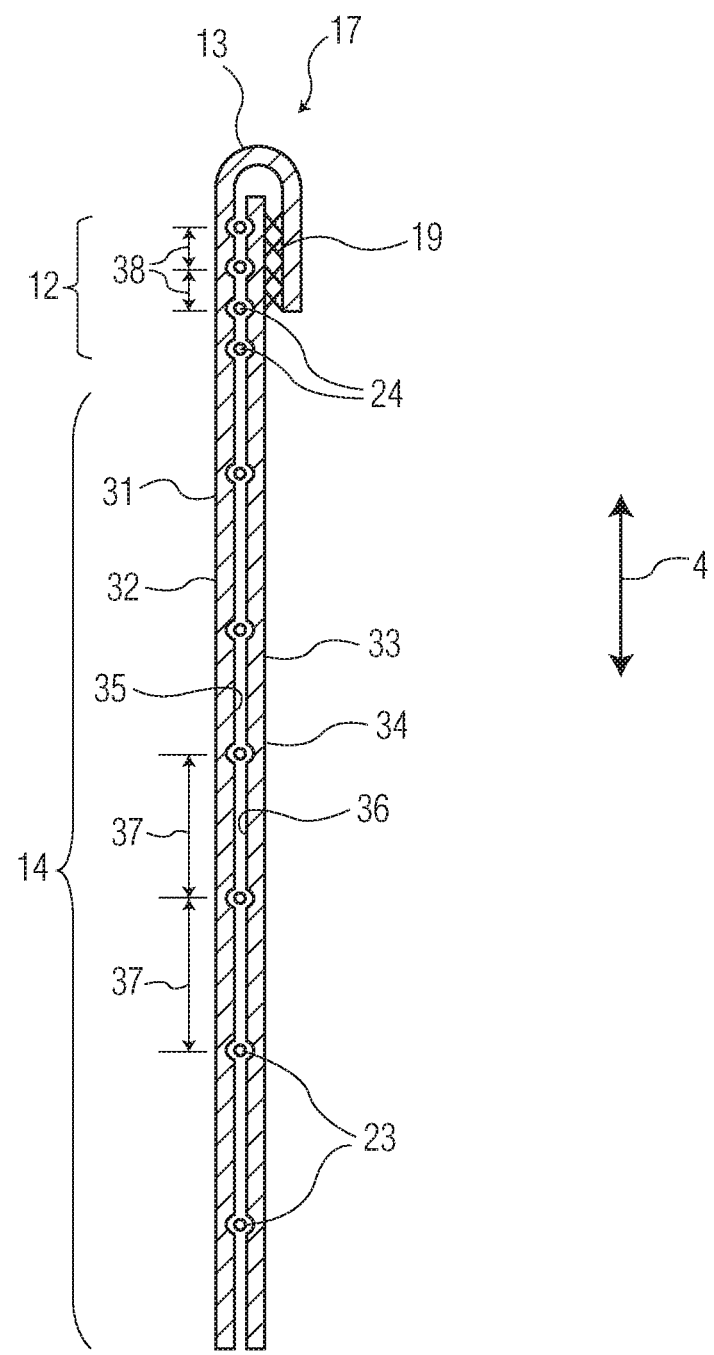
FIG. 3A is a first exemplary cross-section of the article of FIG. 1 as viewed along line 3-3.

FIG. 3A depicts an exemplary cross-section of the article 10 of FIG. 1 as viewed along the line 3-3 through the front waistband region 12 and the front chassis region 14. In the embodiment of FIG. 3A, the front chassis region 14 is seen extending in the longitudinal direction 4 and comprising an outer front chassis web material 31 and an inner front chassis web material 33, with elastomeric strands 23 disposed therebetween. In the embodiment of FIG. 3A, the front waistband region 12 comprises the same outer front chassis web material 31 and the same inner front chassis web material 33, but with elastomeric strands 24 disposed therebetween. Although not shown, the rear chassis region 18 and the rear waistband region 20 may be constructed in a similar manner to the front chassis region 14 and the front waistband region 12, respectively, as described below.

In the embodiment of FIG. 3A, the front waist edge 13 is formed by a fold 17, where the outer front chassis web material 31 is longer in the longitudinal dimension than the inner front chassis web material 33 and is folded over the inner front chassis web material 33 and bonded to an inner surface 34 of the inner front chassis web material 33 through attachment region 19. Attachment region 19 may be formed by adhesives, or through direct bonding of outer front chassis web material 31 to inner front chassis web material 33, such as by heat, pressure, and/or ultrasonic energy. It should be understood, however, that in other embodiments, the inner front chassis web material 33 may be longer than the outer front chassis web material 31, and the fold 17 may be formed by folding the inner front chassis web material 33 over the outer front chassis web material 31 and bonding the inner front chassis web material 33 to an outer surface 32 of the outer front chassis web material 31. In still other embodiments, the front waist edge 13 may not be formed by any fold. Rather, the outer front chassis web material 31 and the inner front chassis web material 33 may be approximately equal in length and an outer surface 36 of the inner front chassis web material 33 may be bonded to an inner surface 35 of the outer front chassis web material 31, for example through an adhesive, or through heat, pressure, and/or ultrasonic energy.

In general, the outer front chassis web material 31 and the inner front chassis web material 33 may be constructed of any materials suitable for use in chassis and waistbands, or any other body-contacting portions of clothing garments and absorbent articles. In some particular embodiments, the web materials 31, 33 may comprise any of the suitable web materials described above in relation to a bodyside liner material and/or an outer cover material. The web materials 31, 33 may also be constructed of the same material or different materials. Additionally, although only shown as a single layer in FIGS. 3A, 3B, each of the web materials 31, 33 may comprise a single layer, multiple layers, laminates, or the like in different contemplated embodiments.

Exemplary suitable classes of materials for the web materials 31, 33, include synthetic fibers (for example, polyethylene or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Additionally, various woven and non-woven fabrics can be used for the web materials 31, 33. The web materials 31, 33 can comprise woven fabrics, nonwoven fabrics, polymer films, film-fabric laminates or the like, as well as combinations thereof. Examples of nonwoven fabrics can include spunbond fabrics, meltblown fabrics, coform fabrics, carded webs, bonded-carded webs, bicomponent spunbond fabrics, spunlaces, or the like, as well as combinations thereof.

For example, the web materials 31, 33 can be composed of a meltblown or spunbond webs of polyolefin fibers. Alternatively, the web materials 31, 33 can be bonded-carded webs composed of natural and/or synthetic fibers. The web materials 31, 33 can be composed of a substantially hydrophobic materials, and the hydrophobic materials can, optionally, be treated with a surfactant or otherwise processed to impart a desired level of wettability and hydrophilicity. The surfactant can be applied by any conventional means, such as spraying, printing, brush coating or the like. The surfactant can be applied to the entirety of the web materials 31, 33 or it can be selectively applied to particular sections of the web materials 31, 33. Some specific exemplary materials suitable for the web materials 31, 33 include 100% polypropylene bonded-carded webs in the 5-150 gsm range. Other exemplary suitable materials include spunbond polypropylene non-woven webs in the 5-150 gsm range. In particularly preferential embodiments, the basis weights may be in the 5-30 gsm range. Still other exemplary materials may have basis weights above 150 gsm.

In an embodiment, the web materials 31, 33 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, the web materials 31, 33 can be spunbond substrates with a basis weight from about 8 to about 50 gsm. In an embodiment, the web materials 31, 33 can be a 12 gsm spunbond-meltblown-spunbond substrate. In another embodiment, the web materials 31, 33 can be an 8 gsm spunbond-meltblown-spunbond substrate.

Suitable elastomeric materials for the elastomeric strands 23, 24 can include, but are not limited to, spandex elastomeric strands, strands of natural or synthetic rubber, thermoplastic elastomeric materials, or heat activated elastomeric materials. The elastomeric strands 23, 24 can be any elastomeric material capable of being elongated at least about 50 percent, desirably about 350 percent, and capable of recovering to within at least about 250 percent, and desirably about 150 percent of its original length after being elongated about 300 percent. The elastomeric strands 23, 24 can be a spandex elastomeric strand(s), or polyurethane-based synthetic fibers, such as LYCRA. Alternatively, the elastomeric strands 23, 24 can be composed of a thermoplastic elastomer or a natural or a synthetic rubber, or even a heat activated elastic material, which can be activated with heat treatment after the elastomeric strands 23, 24 have been disposed between the web materials 31, 33 and the web materials 31, 33 have been bonded together. In general, any suitable elastic material may be used for strands 23, 24. In at least some embodiments, the elastomeric strands may have diameters that range between about 10 denier to about 1500 denier.

The front chassis region 14 and the front waistband region 12 may be defined by the number and location of the elastomeric strands 23, 24 within the front region 7 of the article 10. In the embodiments of the present disclosure, the front waistband region 12 comprises the four (4) elastomeric strands disposed longitudinally closest to the front waist edge 13, which are labeled as elastomeric strands 24. The front chassis region 14 comprises the rest of the elastomeric strands disposed within the front region 7 of the absorbent article 10, which are labeled as elastomeric strands 23. These definitions are the same for the rear chassis region 18 and the rear waistband region 20, as well.

As described previously, in order to differentiate visually between the front waistband region 12 and the front chassis region 14, one or more parameters may differ between the two regions 12, 14. In the example of FIG. 3A, it can be seen that one parameter that differs between the regions 12, 14 is the longitudinal spacing of the strands 23, 24 within each region 12, 14. For example, the front chassis region 14 comprises elastomeric strands 23 which have a first longitudinal spacing 37, while the front waistband region 12 comprises elastomeric strands 24 which have a second longitudinal spacing 38 which differs from the first longitudinal spacing 37. In such an embodiment, the front waistband region 12 may comprise the sharper, more definite pattern while the front chassis region 14 comprises the more indistinct, blousy pattern. It should be understood that the spacing between each of the strands 23, 24 within the regions 12, 14 does not need to be the same. Rather, the first longitudinal spacing 37 and the second longitudinal spacing 38 may represent an average of all of the longitudinal spacings between the strands 23, 24 within each of the regions 12, 14. For example, a longitudinal spacing measurement may be taken for between each adjacent strand 24 within the front waistband region 12. The second longitudinal spacing parameter 38 may then be an average of these gathered longitudinal measurements. This second longitudinal spacing parameter 38 may be compared to the first longitudinal spacing parameter 37 that is formed in the same way for the front chassis region 14.

It has been found that sharper, more definite patterns are produced when the spacing between elastomeric strands is less than 8 mm, or more preferably less than 7.5 mm, more preferably less than 7 mm, more preferably less than 6.5 mm, more preferably less than 6 mm, more preferably less than 5.5 mm, more preferably less than 5 mm, more preferably less than 4.5 mm, and even more preferably less than 4 mm. Accordingly, in embodiments where the front waistband region 12 comprises the sharper, more definite pattern, the second longitudinal spacing 38 can be any of the above described spacings. Additionally, in order to produce greater visual distinction between the regions 12, 14, it has been found that the first longitudinal spacing 37 should be greater than the second longitudinal spacing 38 by at least 1 mm, or more preferably by at least 1.5 mm, more preferably by at least 2 mm, more preferably by at least 2.5 mm, more preferably by at least 3 mm, more preferably by at least 3.5 mm, more preferably by at least 4 mm, or even more preferably by at least 4.5 mm.

As an alternative to having varied longitudinal spacing between the strands 23, 24, the installed elongation of the strands 23, 24 may be varied in order to produce a visually different pattern between the regions 12, 14. The installed elongation is a measure of the amount of strain at which the strand is under when it is applied to the article 10, or a precursor component of the article 10. For example, a 100 mm length of an elastomeric strand which has been stretched to 150 mm has an installed elongation of 50% ((150/100)−1)×100%). It has been found that higher installed elongation of elastomeric strands, such as strands 23, 24, produces less-defined, blousy visual patterns. Accordingly, where the front waistband region 12 comprises the sharper, more definite pattern, the elastomeric strands 24 may have a lower installed elongation than the elastomeric strands 23 of the front chassis region 14, which comprises the more indistinct, blousy pattern.

It has been found that more indistinct, blousy patterns can be achieved with strands having installed elongations greater than or equal to at least 150%, or more preferably greater than or equal to at least 175%, more preferably greater than or equal to at least 200%, more preferably greater than or equal to at least 225%, more preferably greater than or equal to at least 250%, or even more preferably greater than or equal to at least 300%. Accordingly, where the front chassis region 14 comprises the sharper, more definite pattern, the elastomeric strands 23 may have any of the above described installed elongations. Additionally, in order to produce more visual distinctions between the front waistband region 12 and the front chassis region 14, the elastomeric strands 23 of the front chassis region 14 may have installed elongations greater than the installed elongation of the elastomeric strands 24 by at least 25%, or more preferably by at least 50%, more preferably by at least 75%, more preferably by at least 100%, more preferably by at least 125%, more preferably by at least 150%, or even more preferably by at least 200%. It should also be understood each of the elastomeric strands 23, 24 do not need to have the same installed elongation as each of the other strands 23, 24 within the regions 12, 14. Rather, when comparing the installed elongation value of the strands 23, 24 between the regions 12, 14 an average installed elongation metric may be used. For example, the installed elongation of each of the strands 24 within the front waistband region 12 may be averaged and the installed elongation of each of the strands 23 within the front chassis region 14 may be averaged. These averaged installed elongations may then be compared to determine which of the regions 12, 14 has a higher or lower average installed elongation.

Of course, in at least some contemplated embodiments where the front waistband region 12 comprises the sharper, more definite pattern, the strands 24 of front waistband region 12 may have both a longitudinal spacing 38 that is less than the longitudinal spacing 37 of the strands 23 and a lower installed elongation than the installed elongation of the strands 23. In further embodiments, however, the strands 24 may have a lower strand spacing 38 than the spacing 37 of the strands 23 but a higher installed elongation, or a higher strand spacing 38 than the strand spacing 37 but a lower installed elongation. In such embodiments, the amount of difference between the strand spacings 37, 38 and the installed elongations of the strands 23, 24 may be chosen to produce the desired visual effect of the front waistband region 12 having the sharper, more definite pattern and the front chassis region 14 having the more indistinct, blousy pattern.

As an alternative to having varied longitudinal spacing or installed elongation between the strands 23, 24, the decitex of the strands 23, 24 may be varied in order to produce a visually different pattern between the regions 12, 14. It has been found that a higher decitex allows for sharper, more definite patterns where the other parameters are held constant. Accordingly, where the front waistband region 12 comprises the sharper, more definite pattern, the elastomeric strands 24 may have a relatively higher decitex in order to produce a sharper, more definite pattern at a given strand spacing and installed elongation while the strands 23 have a relatively lower decitex which at the given strand spacing and installed elongation produces a more indistinct, blousy pattern.

It has been found that sharper, more definite patterns can be achieved with strands having a decitex greater than about 470, or more preferably greater than about 545, more preferably greater than about 620, more preferably greater than about 695, more preferably greater than about 770, more preferably greater than about 845, more preferably greater than about 920, or even more preferably greater than about 995. Accordingly, where the front waistband region 12 comprises the sharper, more definite pattern, the elastomeric strands 24 may have any of the above described decitexes. Additionally, in order to produce more visual distinctions between the front waistband region 12 and the front chassis region 14, the elastomeric strands 23 of the front chassis region 14 may have a decitex which is greater than the decitex of the strands 24 by at least 50, or more preferably by at least 100, more preferably by at least 150, more preferably by at least 200, more preferably by at least 250, more preferably by at least 300, more preferably by at least 350, more preferably by at least 400, or even more preferably by at least 450. It should also be understood each of the elastomeric strands 23, 24 do not need to have the same decitex as each of the other strands 23, 24 within the regions 12, 14. Rather, when comparing the decitex value of the strands 23, 24 between the regions 12, 14 an average decitex value may be used for each region. These average decitex values for the regions 12, 14 may comprise an average of the decitex values of all of the strands 24 within the front waistband region 12 and the average of the decitex values of all of the strands 23 within the front chassis region 14.

Of course, in at least some contemplated embodiments where the front waistband region 12 comprises the sharper, more definite pattern, the strands 24 of front waistband region 12 may have all of a longitudinal spacing 38 that is less than the longitudinal spacing 37 of the strands 23 in the region 14, a lower installed elongation than the installed elongation of the strands 23, and strands 24 may have higher decitexes than the strands 23. In further embodiments, however, the strands 24 may have a higher installed elongation but a higher decitex than the strands 23, or a lower decitex but a lower installed elongation. In further embodiments, the strands 24 may have a lower strand spacing 38 than the strand spacing 37 of the strands 23 but a lower decitex, or a higher strands spacing 38 but a higher strand decitex than the strands 23. In still other contemplated embodiments, the strands 24 may have a higher spacing 38 than the spacing 37 of the strands 23, a higher installed elongation than the strands 23, but also a higher decitex. Alternatively, the strands 24 may have a higher spacing 38 than the spacing 37 of the strands 23, a lower decitex than the strands 23, but also a lower installed elongation than the strands 23. In still more alternative embodiments, the strands 24 may have a lower spacing 38 than the spacing 37 of the strands 23, but a higher installed elongation and also a lower decitex than the strands 23. In any of these embodiments, the amount of difference between the strand spacings 37, 38, the installed elongations, and the decitexes of the strands 23, 24 may be chosen to produce the desired visual effect of the front waistband region 12 having the sharper, more definite pattern and the front chassis region 14 having the more indistinct, blousy pattern.

In some contemplated embodiments of the present disclosure, it may be more preferable for the front chassis region 14 to comprise the sharper, more definite pattern and the front waistband region 12 to comprise the more indistinct, blousy pattern. In such embodiments, all of the configurations of the strand spacings 37, 38, the installed elongations, and/or the decitexes described previously in relation to the embodiments where the front waistband region 12 comprised the sharper, more definite pattern and the front chassis region 14 comprised the more indistinct, blousy pattern may be reversed. For instance, the front chassis region 14 may comprise any of the above described configurations of the strand spacings 37, 38, installed elongations, and/or strand decitexes which produce the relatively sharper, more definite pattern while the front waistband region 12 may comprise any of the above described configurations of the strand spacings 37, 38, installed elongations, and/or strand decitexes which produce the more indistinct, blousy pattern. In still further embodiments, as described with respect to FIG. 1, the configuration of the strand spacings 37, 38, installed elongations, and/or strand decitexes of the front chassis region 14 may be different than the rear chassis region 18 such that the front chassis region 14 comprises the sharper, more definite pattern and the rear chassis region 18 comprises the more indistinct, blousy pattern. The opposite may be true in other embodiments. Additionally, the configuration of the strand spacings 37, 38, installed elongations, and/or strand decitexes of the front waistband region 12 may be different than the rear waistband region 20 such that the front waistband region 12 comprises the sharper, more definite pattern and the rear waistband region 20 comprises the more indistinct, blousy pattern. The opposite may be true in other embodiments. All combinations of which of the front waistband region 12, the front chassis region 14, the rear chassis region 18, and the rear waistband region 20 comprise the sharper, more definite pattern and which comprise the more indistinct, blousy pattern are contemplated by the present disclosure.

Figure 3B:
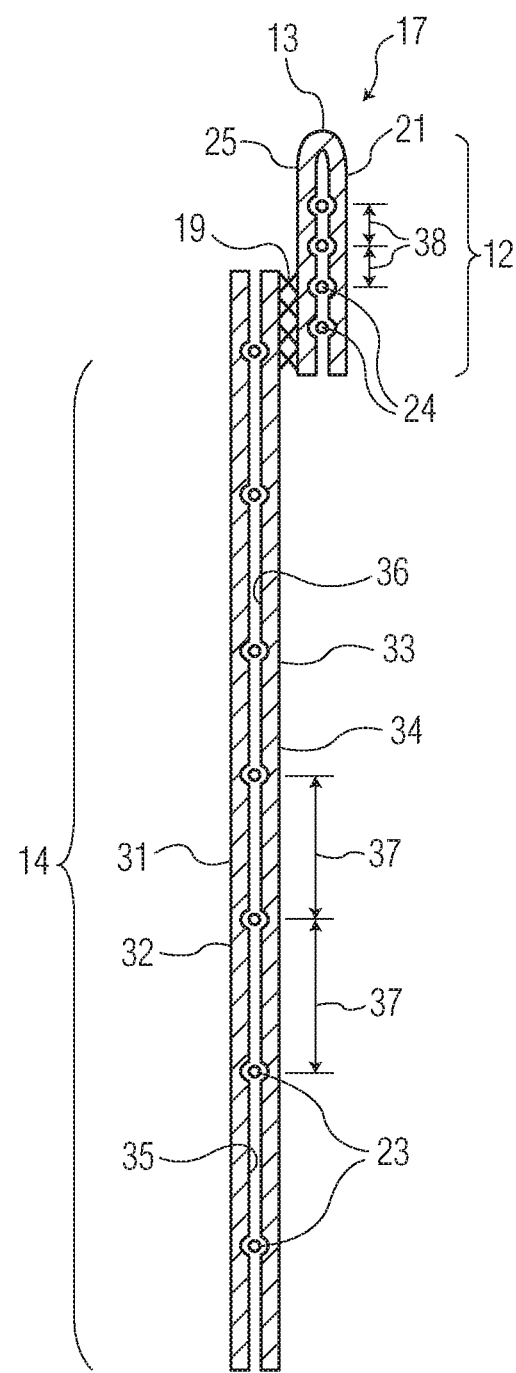
FIG. 3B is a second exemplary cross-section of the article of FIG. 1 as viewed along line 3-3.

FIG. 3B depicts an alternative exemplary cross-section of the article 10 of FIG. 1 taken along line 3-3 through the front waistband region 12 and the front chassis region 14. In contrast to the embodiment of FIG. 3A, the embodiment of FIG. 3B depicts the front waistband region 12 comprising a front waistband component 21 that is formed separately from the front chassis region 14. The waistband component 21 is coupled to the front chassis region 14 through attachment region 19 attaching the front waistband component 21 to the inner surface 34 of the inner web material 33. The attachment region 19 may comprise an adhesive, or the front waistband component 21 may be directly attached to the inner web material 33 using heat, pressure, or ultrasonic energy to form the attachment region 19.

As a separate component, the front waistband component 21 may be comprised of a single front waistband web material 25 folded over to sandwich the elastomeric strands 24, as shown in FIG. 3B. Alternatively, the front waistband component 21 may be comprised of an inner front waistband web material and a second front waistband material. In any of these embodiments, the front waistband component 21 may be formed without the use of adhesive, for example by bonding the single front waistband web material 25 to itself (or bonding an inner front waistband web material and a second front waistband material together) with the elastomeric strands 24 disposed therebetween and entrapping the elastomeric strands 24 with bonds, as described previously. Accordingly, the front waistband region 12 and the front chassis region 14 (and rear chassis region 18 and rear waistband region 20) may be configured to have visually different patterns in the same manner as any of the embodiments described previously in relation to FIG. 3A.

Figure 4:
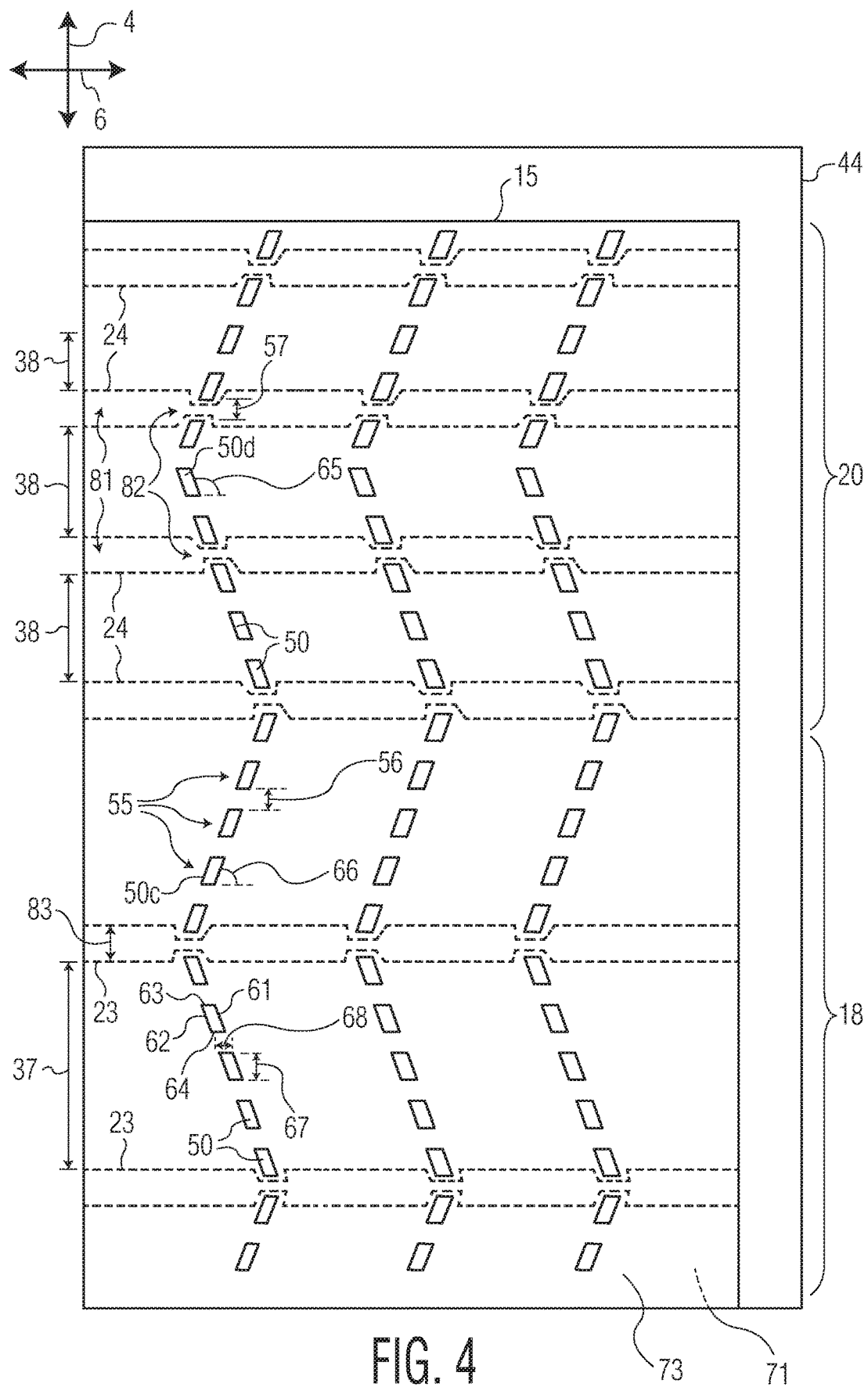
FIG. 4 is a plan view of a close-up of the region 44 of FIG. 2.

FIG. 4 depicts a close-up of the region 44 of FIG. 2 of the rear chassis region 18 and the rear waistband 20 and detailing one particular bond pattern that can be used to produce the visual patterns depicted in FIGS. 1 and 2. The construction of the rear chassis region 18 and the rear waistband region 20 can be similar, and even mirror, the front chassis region 14 and the front waistband region 12 as described above with respect to FIGS. 1-3B. Accordingly, FIG. 4 depicts elastomeric strands 23, 24 which extend through and provide elastic properties to the regions 18, 20, including non-entrapped portions 81 and entrapped portions 82 of the strands 23, 24.

In order to form the chassis and waistband regions 12, 14, 18, and 20, the elastomeric strands 23, 24 may be stretched before or as the strands 23, 24 are positioned between the inner and outer web materials 31, 33 and/or 71, 73. The elastomeric strands 23, 24 have an un-tensioned outer diameter, and the outer diameter of the strands 23, 24 may decrease as the strands 23, 24 are stretched. Accordingly, before or at the time the strands 23, 24 are placed between the inner and outer web materials 31, 33 and/or 71, 73, the elastomeric strands 23, 24 may have an outer diameter that is less than their un-tensioned outer diameter.

While in this stretched state, at least some of the bonds 50 may be placed on opposite sides of the stretched elastomeric strands 23, 24 and spaced apart in the longitudinal direction 4 across the elastomeric strands 23, 24 a longitudinal distance 57. In some embodiments, the longitudinal distance 57 may be approximately equal to the outer diameter of the strands 23, 24 at the time the bonds 50 are formed on opposite sides of the stretched elastomeric strands 23, 24. In other embodiments, the longitudinal distance 57 may be greater than the outer diameter of the strands 23, 24 at the time the bonds 50 are formed on opposite sides of the stretched elastomeric strands 23, 24, but less than the outer diameter of the un-tensioned diameter of the strands 23, 24. The pairs of bonds 50 which are formed on opposite sides of a stretched elastomeric strand 23, 24 may form what is termed herein a bond pair. Such bond pairs are comprise longitudinally adjacent bonds of the bonds 50 for which one of the strands 23, 24 extend therebetween. These bond pairs form the bonds which "entrap" the strands 23, 24, thereby affixing them to the web materials 71, 73 (and 31, 33 in the front region 7).

As the elastomeric strands 23, 24 are allowed to relax, the outer diameter of the elastomeric strands 23, 24 generally increases back toward their un-tensioned outer diameter. However, as can be seen in FIG. 4, this expansion is inhibited in the entrapped portions 82 of the elastomeric strands 23, 24 by the pairs of bonds 50 which form bond pairs, whereby the bonds 50 of the bond pairs are positioned across the strands 23, 24 a longitudinal distance less than the un-tensioned diameter of the strands 23, 24. As the strands 23, 24 relax and contract from their stretched state, the non-entrapped portions 81 of the elastomeric strands 23, 24 expand in the longitudinal direction 4 (e.g. the outer diameter of the elastomeric strands 23, 24 increases), resulting in the structure as seen in FIG. 4 with the strands 23, 24 shown having expanded outer diameter 83 in the non-entrapped portions 81.

In some embodiments, the expanded diameter 83 may be the same as the un-tensioned diameter of the strands 23, 24, but in other embodiments this may not be the case. For example, the specific configuration of the type of elastomeric material used to form strands 23, 24, the amount by which the strands 23, 24 are elongated in the forming process, and the location of the bonds 50 of the bond pairs in relation to the elongated strands 23, 24, both in the longitudinal distance 57 between bonds 50 of the bond pairs and in the lateral distance between laterally adjacent bonds 50, may prevent the diameter of the strands 23, 24 from expanding in the non-entrapped portions 81 all the way back to their un-tensioned diameters. Accordingly, in some embodiments the expanded diameter 83 in the non-entrapped portions 81 of at least some of the elastomeric strands 23, 24 may still be less than their un-tensioned diameters.

The bonds 50 can be formed through any suitable bonding technique, such as thermal/heat bonding, ultrasonic bonding, pressure bonding, or other known bonding techniques. In general, as will be described in more detail below, the bonds 50 can be formed by use of a pattern component and a smooth component. To form the bonds 50, the web materials 31, 33 and/or 71, 73, with the elastomeric strands 23, 24 disposed therebetween, are positioned between the pattern component and the smooth component with appropriate alignment between any features of the pattern component and the elastomeric strands 23, 24. For instance, the elastomeric strands 23, 24 may be positioned between raised protrusions of the pattern component.

Where thermal bonding, pressure bonding, or rotary ultrasonic bonding techniques are used to form the bonds 50, the pattern component and the smooth component may be pattern rolls and smooth rolls, respectively. In such embodiments, the pattern rolls may contain a number of raised portions that protrude from the surface of the pattern rolls. The raised portions may correspond approximately with the shape of the bonds 50 and aligned on the surface of the pattern rolls to produce the longitudinal and latitudinal alignment of the bonds 50 as depicted in the different embodiments of the elasticated materials of the present disclosure. The smooth rolls may generally be solid rolls with smooth outer surfaces.

The heat bonding techniques which may be used to form the bonds 50 may include heating the raised portions of the pattern rolls to between about 70 degrees C. and about 340 degrees C. In general, the level of heating should be less than that which results in melting of the elastic strands 23, 24 when the bonds 50 are being formed. While the raised portions are at the appropriate temperature, the pattern roll may be pressed onto the smooth roll, with the layers 31, 33 and/or 71, 73 and the elastomeric strands 23, 24 positioned between the rolls. As some examples, the nip pressure (hertzian contact pressure) used to form the bonds 50 in such embodiments may be between about 500 KPa and about 2,750 KPa, and the layers 31, 33 and/or 71, 73 and the elastomeric strands 23, 24 may pass between the pattern and anvil rolls between about 100 linear meters per minute (mpm) and about 350 (mpm). Of course, other suitable values may be used in other embodiments.

The rotary ultrasonic bonding techniques that may be used to form the bonds 50 may use ultrasonic energy in order to form the bonds 50. For instance, as the layers 31, 33 and/or 71, 73 and the elastomeric strands 23, 24 pass between the pattern roll and smooth roll of a rotary ultrasonic bonder, the smooth roll may be vibrated at a frequency of between about 20,000 Hz and about 50,000 Hz, causing internal heating of the layers 31, 33 and/or 71, 73 to such an extent that the layers 31, 33 and/or 71, 73 melt together forming the bonds 50.

The pressure bonding techniques which may be used to form the bonds 50 may be similar to the heat bonding techniques described above, except that no external heat may need to be applied to the raised portions of the pattern roll. However, in order to compensate for the raised portions only being at an ambient temperature, the nip pressure (hertzian contact pressure) between the pattern roll and the smooth roll to form the bonds 50 must be greatly increased. In some examples, the nip pressure (hertzian contact pressure) may be between about 500 MPa and about 1500 MPa, while the layers 31, 33 and/or 71, 73 and the elastomeric strands 23, 24 pass between the pattern roll and the anvil roll at between about 150 mpm and 450 mpm. Of course, other suitable values may be used in other embodiments.

In non-rotary ultrasonic bonding techniques that may be used to form the bonds 50, the pattern element and the anvil element may be a smooth ultrasonic horn and a patterned anvil. In such embodiments, the anvil component may have the raised portions, while the ultrasonic horn has a generally smooth surface. Like with the rotary ultrasonic techniques, the ultrasonic horn may be vibrated at a frequency of between about 20,000 Hz and about 50,000 Hz, as the layers 31, 33 and/or 71, 73 and the elastomeric strands 23, 24 pass between the ultrasonic horn and the patterned anvil. This ultrasonic energy application causes internal heating of the layers 31, 33 and/or 71, 73 to such an extent that the layers 31, 33 and/or 71, 73 melt together forming the bonds 50.

In general, such heat bonding techniques, ultrasonic bonding techniques, and pressure bonding techniques are known in the art. It should be understood that the parameters described for the different techniques are only exemplary suitable parameters. The described techniques may be used to form the bonds 50 using such techniques operating with other suitable parameters, as is known in the art. For instance, PCT Patent Application WO 2010/068150, titled "METHOD AND APPARATUS FOR BONDING", which is incorporated herein by reference in its entirety, details methods and apparatus for performing pressure bonding which could be used to form the bonds 50 of the bond patterns described in the present disclosure using many different suitable parameters. It should additionally be understood that the different ways in which the bonds 50 are formed do not appreciably affect the resulting structure of the elasticated material, aside from possibly resulting in different strengths of bonds. However, all of such known techniques are capable of producing bonds which are strong enough to resist the expansion of the elastomeric strands positioned between the bonds without breaking. Accordingly, the bonds 50 may be formed according to any known bonding technique without departing from the scope of the present disclosure.

FIG. 4 further depicts details of the bonds 50 which bond an outer rear chassis web material 71 and an inner rear chassis web material 73 together and entrapping the strands 23, 24 between the web materials 71, 73. The bonds 50 may each include a first side portion 61, a second side portion 62 opposite the first side portion 61, a top portion 63, and a bottom portion 64 opposite the top portion 63. In embodiments where the bonds 50 have generally linearly extending side portions 61 and 62, these side portions 61, 62 may extend at least partially in the longitudinal direction 4.

In general, the bonds 50 may have any suitable size or shape. However, in at least some embodiments, the bonds 50 may range between about 50 square micrometers to about 20 square millimeters, or between about 70 square micrometers to about 10 square millimeters, or between about 250 square micrometers and about 5 square millimeters. Additionally, in some embodiments, the dimension of the bonds 50 in a direction generally parallel to the elastomeric strands 23, 24, e.g. the dimension of the top and bottom portions 63, 64, may be between about two times to about six times greater than the dimension of the side portions 61, 62 of the bonds 50. For instance, in the embodiment of FIG. 4, a length of the top or bottom portions 63, 64 may be between about two times and about six times greater than a length of a side portion 61 or 62.

Although shown as generally rectangular, and more specifically as parallelograms, the bonds 50 may be any suitable shape. For instance, the bonds 50 may be circular, semicircular, oval shaped, half-oval shaped, triangular, square, rectangular, trapezoidal, rhombus-shaped, or the like. In some embodiments, the bonds 50 can have three sides, four sides, five sides, six sides, or any other suitable number of sides.

The bonds 50 may be arranged into a series of generally parallel rows 55 which extend in the direction in which the strands 23, 24 extend. In some embodiments, longitudinally adjacent rows 55 may be spaced apart in the longitudinal direction 4 a distance 56. In some particular embodiments, each of the rows 55 may be spaced apart that same distance 56, and the distance 56 may be less than an un-tensioned diameter of the strands 23, 24. Accordingly, the strands 23, 24 may be able to be entrapped between any of the rows 55, and the longitudinally adjacent bonds of the bonds 50 of longitudinally adjacent rows 55 for which a strand 23, 24 extends therebetween would form bond pairs. However, in other embodiments, some of the rows 55 may be spaced apart the distance 56, while other of the rows 55 may be spaced apart a distance 57 which is different than the distance 56. In such embodiments, the distance 56 may be greater than the un-tensioned diameter of the strands 23, 24 while the distance 57 may be less than the un-tensioned diameter of the strands 23, 24. In such embodiments, then, the strands 23, 24 may be only positioned between rows 55 which are spaced apart the distance 57 to ensure that the strands 23, 24 are entrapped within the region 18, 20.

However, where the distance 56 is greater than the un-tensioned diameter of the strands 23, 24, it is important for the distance 56 to not be too large. If the distance 56 is greater than about 2 mm in some embodiments, or greater than about 1.5 mm in some embodiments, or greater than about 1 mm in some embodiments, or greater than about 0.75 mm in some embodiments, or greater than about 0.5 mm in some embodiments, the visual sharpness and definiteness of any pattern may be reduced relative to embodiments where the distance 56 is less than any of the above values. Accordingly, where it is desired that one or more of the regions 12, 14, 18, and 20 have a relatively sharp, definite pattern, a spacing 56 between adjacent rows 55 in such regions (e.g. adjacent rows 55 for which one of the strands 23, 24 does not extend therebetween) may be less than 2 mm, or less than 1.5 mm, or less than 1 mm, or less than 0.75 mm, or less than 0.5 mm in various different embodiments. Conversely, where it is desired that one or more of the regions 12, 14, 18, and 20 have a relatively more indistinct, blousy pattern, a spacing 56 between adjacent rows 55 in such regions (e.g. adjacent rows 55 for which one of the strands 23, 24 does not extend therebetween) may be greater than 0.5 mm, or greater than 0.75 mm, or greater than 1 mm, or greater than 1.5 mm, or greater than 2 mm in various different embodiments. In particular embodiments where it is desired to produce a visual difference in a pattern of a first one of the regions 12, 14, 18, 20 relative to a pattern of a second one of the regions 12, 14, 18, 20, the spacing 56 between the rows 55 in the first one of the regions 12, 14, 18, 20 may be greater than the spacing 56 between the rows 55 in the second one of the regions 12, 14, 18, 20 by about 0.5 mm, about 0.75 mm, about 1 mm, about 1.25 mm, about 1.5 mm, about 1.75 mm, about 2 mm, or about 2.25 mm, or any other suitable value. Additionally, it is not necessary that each of the spacings 56 within the first or second of the regions 12, 14, 18, 20 be the same. Rather, when comparing the spacing 56 between a first of the regions 12, 14, 18, 20 and a second of the regions 12, 14, 18, 20, an average value of the spacings 56 in each of the first and second region may be used in such a comparison.

In addition to having differing longitudinal spacings between the rows 55, e.g. spacings 56 and 57 or even different spacings 56 between rows 55 within a same one of the regions 12, 14, 18, 20, a spacing between bonds 50 in the lateral direction 6 within a given row 55 may differ, both within a row 55 and between different of the rows 55. For example, a lateral spacing between adjacent bonds within the same row may differ between a row 55 which is adjacent one of the strands 23, 24 and a row 55 which is not adjacent one of the strands 23, 24. Alternatively, or additionally, other embodiments may have rows 55 with bonds 50 where the lateral spacing between laterally adjacent bonds varies within the row 55. For example, the lateral spacing between bonds 50 within a given row 55 may vary throughout different lateral regions of a garment in order to impart a desired pattern (or lack thereof) or softness.

In additional or alternative embodiments to any of those described above, the first side portions 61 of the bonds 50 may be angled with respect to the direction in which the elastomeric strands 23, 24 extend, for example the lateral direction 6 in FIG. 4. The first side portion 61 of bond 50c can be seen forming angle 66 with respect to the lateral direction 6 in FIG. 4. Angling of the first side portions 61 of the bonds 50 may be beneficial in order to more effectively form the bonds 50 and/or to provide the chassis and/or waistband regions 12, 14, 18, 20 with desirable stretch properties. In such embodiments, the angle 66 may range anywhere between about 0 degrees and about 180 degrees. In some more specific embodiments, the angle 66 may range between about 15 degrees and about 90 degrees, or between about 30 degrees and about 89 degrees, or between about 50 degrees and about 88 degrees. In other embodiments, the angle 66 may range between about 105 degrees and about 180 degrees, or between about 120 degrees and about 179 degrees, or between about 140 degrees and about 178 degrees.

In some embodiments where the first side portions 61 of at least some of the bonds 50 form an angle 66 with respect to the direction in which the elastomeric strands 23, 24 extend, all or substantially all of the bonds 50 may form the angle 66 with respect to the direction in which the elastomeric strands 23, 24 extend. However, as shown in FIG. 4, in other embodiments a first number of the bonds 50 may have first side portions 61 which form an angle 66 with respect to the direction in which the elastomeric strands 23, 24 extend while a second number of the bonds 50 may have first side portions 61 which form an angle 65 (for example, as shown by bond 50d) with respect to the direction in which the elastomeric strands 23, 24 extend. In such embodiments, the angle 66 may differ from the angle 65. The angle 65 may have any of the possible values described previously with respect to the angle 66, and in some particular embodiments, the angle 65 may be equal to 180 minus the value (in degrees) of the angle 66. For instance, if the angle 66 is 60 degrees, the angle 65 would then be 120 degrees.

In particular embodiments, the regions 12, 14, 18, and/or 20 may comprise a series of rows 55 which have bonds 50 with first side portions 61 forming alternating angles 65 and 66 with respect to the direction in which the strands 23, 24 extend (as seen in FIG. 4). In this manner, the zig-zag pattern depicted in FIGS. 1-4 may be formed. However, it should be understood that other patterns may be formed according the present disclosure. For instance, the particular pattern formed is generally dictated by the parameters of the bonds, such as their size, shape and location within the regions 12, 14, 18, and 20. However, the relative visual sharpness and definiteness or blousy-ness and indistinctiveness of a region 12, 14, 18, and 20 is determined according to the parameters described previously, such as the strand spacing, installed elongation, decitex, and the like. Accordingly, the depicted zig-zag pattern is only one of many that may be formed for which visual differences may be formed according to the present disclosure.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

Those skilled in the art will recognize that the present disclosure may be manifested in a variety of forms other than the specific embodiments described and contemplated herein. Specifically, the various features described with respect to the various embodiments and figures should not be construed to be applicable to only those embodiments and/or figures. Rather, each described feature may be combined with any other feature in various contemplated embodiments, either with or without any of the other features described in conjunction with those features. Accordingly, departure in form and detail may be made without departing from the scope of the present disclosure as described in the appended claims.

The invention claimed is:

1. An absorbent article extending in a longitudinal direction and in a lateral direction, the absorbent article comprising:
a front region having a front waist edge and comprising an elasticated front chassis region and an elasticated front waistband region;
a rear region having a rear waist edge;
a crotch region extending between the front region and the rear region; and
an absorbent body disposed at least partially within the crotch region,
wherein:
the elasticated front chassis region comprises a plurality of elastomeric strands disposed between a first front chassis web material and a second front chassis web material,
the first front chassis web material is bonded to the second front chassis web material by a plurality of discrete bonds arranged in longitudinally adjacent bond rows within the elasticated front chassis region, the plurality of elastomeric strands disposed between some of the longitudinally adjacent bond rows and not disposed between other of the longitudinally adjacent bond rows, and with at least some of the discrete bonds of longitudinally adjacent bond rows having an elastomeric strand disposed therebetween forming bond pairs spaced apart in the longitudinal direction a distance less than an un-tensioned diameter of the elastomeric strand,
the plurality of elastomeric strands of the elasticated front chassis region are spaced apart in the longitudinal direction a first distance,
the elasticated front waistband region comprises a plurality of elastomeric strands disposed between a first front waistband web material and a second front waistband web material,
the first front waistband web material is bonded to the second front waistband web material by a plurality of discrete bonds arranged in longitudinally adjacent bond rows within the elasticated front waistband region, the plurality of elastomeric strands disposed between some of the longitudinally adjacent bond rows and not disposed between other of the longitudinally adjacent bond rows, and with at least some of the discrete bonds of longitudinally adjacent bond rows having an elastomeric strand disposed therebetween forming bond pairs spaced apart in the longitudinal direction a distance less than an un-tensioned diameter of the elastomeric strand,
the plurality of elastomeric strands of the elasticated front waistband region are spaced apart in the longitudinal direction a second distance, the second distance being less than the first distance
the longitudinally adjacent bond rows within the elasticated front chassis region without an elastomeric strand disposed therebetween are spaced apart in the longitudinal direction a first average row distance
the longitudinally adjacent bond rows within the elasticated front waistband region without and elastomeric strand disposed therebetween are spaced apart in the longitudinal direction a second average row distance, the first average row distance being greater than the second average row distance, and the installed elongation of the plurality of elastomeric strands of the elasticated front waistband region is higher than the installed elongation of the plurality of elastomeric strands of the elasticated front chassis region.

2. The absorbent article of claim 1, wherein the installed elongation of the plurality of elastomeric strands of the elasticated front waistband region is greater than 150%.

3. The absorbent article of claim 1, wherein the installed elongation of the plurality of elastomeric strands of the elasticated front waistband region differs from the installed elongation of the plurality of elastomeric strands of the elasticated front chassis region by at least 50%.

4. The absorbent article of claim 1, wherein the decitex of the plurality of elastomeric strands of the elasticated front waistband region is greater than the decitex of the plurality of elastomeric strands of the elasticated front chassis region.

5. The absorbent article of claim 1, wherein the second distance is less than or equal to 6.5 mm.

6. The absorbent article of claim 1, wherein a majority of the longitudinally adjacent bond rows have bonds forming bond pairs which are spaced apart in the longitudinal direction a distance less than an un-tensioned diameter of an elastomeric strand of the plurality of elastomeric strands.

7. The absorbent article of claim 1, wherein the discrete bonds of the elasticated front chassis region have longitudinally extending first side potions with the longitudinally extending first side potions, wherein the first side portions of at least some of the plurality of discrete bonds have longitudinally extending first side portions which form differing angles with respect to the lateral direction such that series of longitudinally adjacent bonds within the elasticated front chassis region form a zig-zag pattern.

8. The absorbent article of claim 1, wherein the discrete bonds of at least some bond pairs of the elasticated front chassis region have longitudinally extending first side potions with the longitudinally extending first side potion of a first bond of a bond pair forming a first angle with respect to the lateral direction and the longitudinally extending first side potion of a second bond of the bond pair forming a second angle with respect to the lateral direction, and wherein the second angle has a value in degrees that is 180 minus the first angle.

9. An array of absorbent articles comprising:
a first series of absorbent articles comprising:
  a front region having a first front waist edge and comprising an elasticated first front chassis region;
  a first rear region having a first rear waist edge;
  a first crotch region extending between the first front region and the first rear region; and
  a first absorbent body disposed at least partially within the first crotch region,
  wherein:
    the elasticated first front chassis region comprises a first plurality of elastomeric strands disposed between a first front chassis web material and a second front chassis web material of the elasticated first front chassis region,
    the first front chassis web material of the elasticated first front chassis region is bonded to the second front chassis web material of the elasticated first front chassis region by a plurality of discrete bonds each having longitudinally extending first side portions, at least some of the discrete bonds forming bond pairs disposed on opposite sides of an elastomeric strand of the plurality of elastomeric strands of the elasticated first front chassis region and spaced apart in the longitudinal direction a distance less than an un-tensioned diameter of the elastomeric strand,
    the longitudinally extending first side portions of at least some of the plurality of discrete bonds bonding the first front chassis web material to the second front chassis web material of the elasticated first front chassis region form differing angles with respect to the lateral direction such that series of longitudinally adjacent bonds within the elasticated first front chassis region form a zig-zag pattern,
    at least some pairs of longitudinally adjacent discrete bonds of the elasticated first front chassis region which are spaced apart in the longitudinal direction a distance less than a diameter of an elastomeric strand of the plurality of elastomeric strands have longitudinally extending first side potions with the longitudinally extending first side potion of a first bond of a pair of longitudinally adjacent bonds forming a first angle with respect to the lateral direction and the longitudinally extending first side potion of a second bond of the pair of longitudinally adjacent bonds forming a second angle with respect to the lateral direction, and wherein the second angle has a value in degrees that is 180 minus the first angle, and
    the plurality of elastomeric strands of the elasticated first front chassis region are spaced apart in the longitudinal direction a first distance; and
  a second series of absorbent articles comprising:
    a second front region having a second front waist edge and comprising an elasticated second front chassis region;
    a second rear region having a second rear waist edge;
    a second crotch region extending between the second front region and the second rear region; and
    a second absorbent body disposed at least partially within the second crotch region,
    wherein:
      the elasticated second front chassis region comprises a plurality of elastomeric strands disposed between a first front chassis web material and a second front chassis web material of the elasticated second front chassis region,
      the first front chassis web material of the elasticated second front chassis region is bonded to the second front chassis web material of the elasticated second front chassis region by a plurality of discrete bonds each having longitudinally extending first side portions, at least some of the discrete bonds forming bond pairs disposed on opposite sides of an elastomeric strand of the plurality of elastomeric strands of the elasticated second front chassis region and spaced apart in the longitudinal direction a distance less than an un-tensioned diameter of the elastomeric strand,
      the longitudinally extending first side portions of at least some of the plurality of discrete bonds bonding the first front chassis web material to the second front chassis web material of the elasticated second front chassis region form differing angles with respect to the lateral direction such that series of longitudinally adjacent bonds within the elasticated first front chassis region form a zig-zag pattern, at least some pairs of longitudinally adjacent discrete bonds of the elasticated second front chassis region which are spaced apart in the longitudinal direction a distance less than a diameter of an elastomeric strand of the plurality of elastomeric strands have longitudinally extending first side potions with the longitudinally extending first side potion of a first bond of a pair of longitudinally adjacent bonds forming a first angle with respect to the lateral direction and the longitudinally extending first side potion of a second bond of the pair of longitudinally adjacent bonds forming a second angle with respect to the lateral direction, and wherein the second angle has a value in degrees that is 180 minus the first angle, and the plurality of elastomeric strands of the elasticated second front chassis region are spaced apart in the longitudinal direction a second distance, and the second distance is greater than the first distance by at least 2 mm.

\* \* \* \* \*